United States Patent [19]

De Sá et al.

[11] 4,337,123

[45] Jun. 29, 1982

[54] PROCESS FOR THE PRODUCTION OF FUEL ALCOHOL, WITHOUT VINASSE

[75] Inventors: Alvaro De Sá; Jacob M. Luksenberg, both of Rio de Janeiro, Brazil

[73] Assignee: Versa Consultoria Técnica LTDA., CGC, Rio de Janeiro, Brazil

[21] Appl. No.: 182,361

[22] Filed: Aug. 29, 1980

[30] Foreign Application Priority Data

Aug. 31, 1979 [BR] Brazil .................................. 7905624
May 30, 1980 [BR] Brazil .................................. 7905624

[51] Int. Cl.³ .......................... B01D 3/14; B01D 21/01
[52] U.S. Cl. ........................................ 203/19; 203/39; 203/DIG. 13; 210/705; 210/724; 210/725
[58] Field of Search .............................. 210/703–705, 210/723–725; 435/161–163; 568/913, 916–922; 203/19, 39, DIG. 13

[56] References Cited

U.S. PATENT DOCUMENTS 996,763 7/1911 Hess ................................ 203/19
2,320,486 6/1943 Stuart .............................. 210/724

Primary Examiner—Frank Seven
Attorney, Agent, or Firm—Beveridge, DeGrandi & Kline

[57] ABSTRACT

A process for the production of fuel alcohol from fermented plant mashes, without vinasse. In this process alcohol is produced from fermented mashes obtained from diverse raw plant materials. The process introduces a treatment of the mash, after fermentation and before distillation, by which treatment several substances contained in the fermented mash are removed, so that the distillation is fed with a purified beer. Distillation of this beer produces alcohol and does not produce vinasse.

12 Claims, 2 Drawing Figures

PROCESS FOR THE PRODUCTION OF FUEL ALCOHOL, WITHOUT VINASSE

INTRODUCTION

A process for the production of fuel alcohol from fermented plant mashes, especially vegetable mashes, without vinasse is disclosed.

This process may be used not only in new alcohol producing distilleries, but also in existing distilleries, through an adaptation of their existing facilities.

BACKGROUND ART

Processes presently employed for the production of alcohol include the following operational phases: (a) fermentation of the appropriate raw materials, producing the fermented mash or "beer" and (b) distillation of the "beer", obtained by fermentation whereby alcohol is produced.

In a typical known process presently used, fermentable raw material has added thereto yeasts and nutrients and then undergoes fermentation whereby a fermented mash or "beer" is obtained. The beer is then usually centrifuged and thereafter this "beer" is distilled whereby alcohol is obtained and vinasse is separated. The vinasse is a by-product and is basically a suspension of organic and mineral solid substances in water.

The characteristics of the vinasse, resulting from the alcohol production processes that are currently in use, vary according to the raw materials used and according to the process features. However, the solid organic substances contained in the vinasse are generally always approximately 80% of the solids content. The high biochemical oxygen demand (BOD) and chemical oxygen demand (COD) are due to these organic contents. The following properties are typical:

| PROPERTIES OF VINASSE | RAW MATERIAL | | |
|---|---|---|---|
| | Melasse | Sugar Cane | Manioc |
| BOD (g/l) | 25.0 | 16.4 | 18.9 |
| COD (g/l) | 65.0 | 33.0 | 23.4 |
| pH | 4.5 | 4.5 | 4.5 |

Historically, the vinasse slops resulting from the alcohol distillation have been thrown directly into sewers, rivers, lakes, and the like. However, the implementation of the Brazilian national plan for alcohol production now introduces the problem of adequate disposal of the vinasse, which will be produced in enormously increased quantities.

Due to the heavy pollution caused by the discharge of these slops, it will not be possible to go on throwing them directly into the natural water systems (rivers, lakes, lagoons or even the sea). Laws in the United States now prevent such discharge from being carried out. The alternative solution of transporting the resulting vinasse for use as a fertilizer on plantations and farms is not adequate, especially when large quantities of vinasse have to be disposed of. The use of vinasse as a fertilizer is suitable only for certain types of soil and in limited quantities. Moreover, spending fuel for the transportation of large volumes of vinasse represents a serious disadvantage. In order to avoid the disposal of the vinasse by simply throwing it into water or on land, the problem of eliminating this vinasse has to be solved.

An extensive research of the existing publications treating this problem has shown that there does not exist, at this time, a good solution for eliminating the vinasse. Several ways of processing the vinasse are presently being proposed by others, envolving treatment by evaporation, fermentation, etc., for subsequent use as a fertilizer or as a raw material for methane gas generation. The substances contained in the vinasse which can eventually be of use for the production of fertilizers or for other purposes are present in low concentration, as vinasse contains about 90% water. Current procedures of evaporation by heating are consequently uneconomical, as they require large expenditure of energy. According to all information reviewed, processes based on treatment by fermentation of the vinasse are also not economical.

Figure 1:
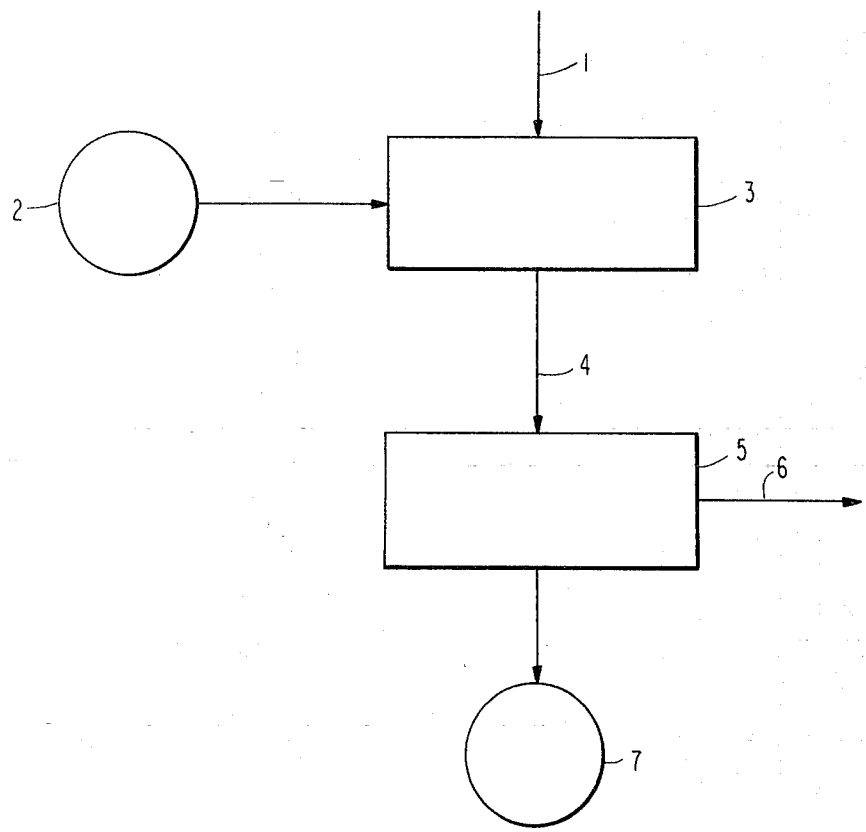
FIG. 1 is a block flow diagram of a prior art process for producing alcohol.

It is known in the prior art according to FIG. 1 to conduct a process wherein fermentable raw material (1), by addition of yeasts and nutrients (2) undergoes fermentation (3) whereby a fermented mash or "beer" (4) is obtained, which is then centrifuged. The "beer" is distilled (5) whereby alcohol (6) is obtained and vinasse (7) is separated.

SUMMARY OF THE INVENTION

The invention presented herein comprises a process for the production of alcohol, from fermented plant mashes, in which no vinasse is produced. This is obtained by treating the fermented mash, after the fermentation phase and before the distillation, by means of which treatment a "purified beer" is obtained; the distillation of this purified beer separates alcohol and a waste which does not present the polluting effects of vinasse. Thus, by combining the treatment with the distillation, a new technical effect is created which allows the production of alcohol without producing vinasse.

DETAILED DESCRIPTION OF THE INVENTION

The present invention is suitable for the processing of fermented mashes obtained by fermentation of any one of numerous fermentable raw plant materials; including but not limited to sugar cane; sugar beets; sorghum starch materials; manioc, potatoes, corn, wheat, rye, etc,; hydrolized cellulosic materials: eucalyptus, pine, sugar cane bagasse, and the like. The process may be applied to mashes fermented by the classical batch fermentation process, to fermented mashes resulting from the Melle-Boinot fermenting process (with re-use of the yeast), or resulting from continuous fermentation processes.

Figure 2:
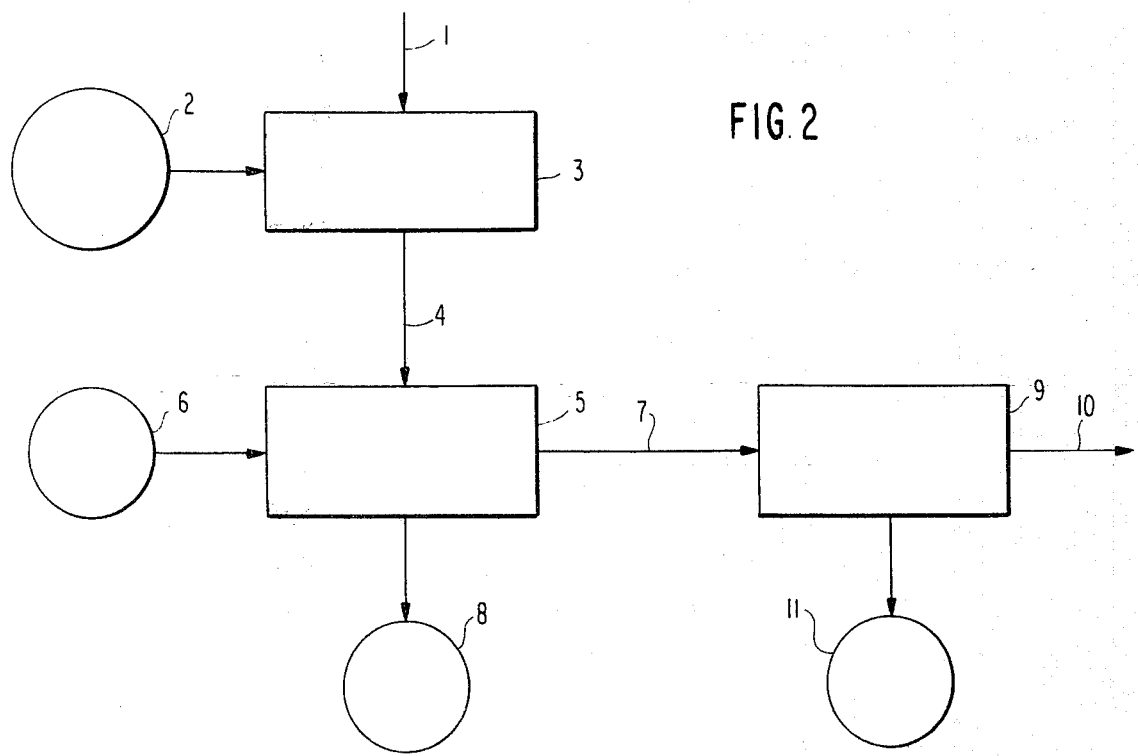
FIG. 2 is a block flow diagram of the process of the invention.

The process herein described presents the following operational phases: (a) fermentation of the raw-materials, resulting in the formation of a fermented mash ("beer") (b) treatment of this "beer", whereby the "purified beer" is obtained, and (c) distillation of this "purified beer", whereby fuel alcohol is obtained. Referring to FIG. 2 the block flow diagram shows the process of the invention, wherein fermentable raw materials (1), by addition of ferment and nutrient substances (2), undergo fermentation (3), the fermented mash ("beer") (4) being obtained; this receives treatment (5) by addition of chemical substances (6) leading to the obtention of the "purified beer" (7) and solid or paste residues (8); the "purified beer" is then taken to the distillation (9) whereby fuel alcohol (10) is obtained and where a waste (11) results, which does not present the polluting effects of vinasse.

Treatment of the fermented mash according to the invention removes, by chemical reactions, flocculation, precipitation, decantation and filtration of the solids in suspension, the undesired contents of the fermented mash; proteins, gums celluloses, starches, dead cells, albuminoid, waxes, fats, solids in suspension, colloids, phosphor salts, nitrogen, potassium, and other undesired substances.

This treatment is performed through a sequence of operations which may vary according to the variable characteristics of the fermented mashes; thus, the treatment may present all or some of the operations listed below, which may or may not be applied in the sequence indicated:

(A) addition of chemical nutrient substances and oxygen (aeration) causing the biological digestion of some substances contained in the fermented mash, by changing the life cycle of the MOG, (yeasts) from respiratory to reproductory; (examples include yeasts)

(B) addition of aluminum or iron salts, in concentrations of 0.01%, to 4%, for elimination of proteins, yeasts, starches, coloring matter, and celluloses, by colloid flocculation; to enhance the floc formation and the settling and clarification, a polyelectrolyte may be used, with reduction of the quantity of coagulant used; (these are flocculating agents)

(C) liming (or neutralization) at temperatures between 60° C. and 105° C., with pH between 7 and 12, made by employing from 0.02% to 4% of calcium hydroxide, ammonium hydroxide or another suitable alkaline material to obtain a neutral or alkaline pH condition. This liming is made in order to remove soluble organic compounds not eliminated by the flocculation, such as hemicelluloses, pentosans, and some organic acids not eliminated by the biological digestion. The neutralization also serves to flocculate the aluminum or iron hydroxides;

(D) separation of the solids in suspension in the liquid ("beer"), with removal of the sedimented matter. as by decantation. Filtration of this matter, wherein the liquid part is separated and returned to the flow;

(E) precipitation by addition of alcohol to the liquid of the substances which can be thus removed, due to the change of composition in the solvent, thereby separating precipitated salts of potassium, ammonium and sodium, among others.

(F) addition of an acid to the liquid, for formation of potassium salts not soluble in water or alcoholic solutions;

(G) neutralization of the "beer", resulting the "second kind of purified beer".

The term "MOG" is understood to mean yeast of the genera: schizosaccharomyces, or zygosaccharomyces, saccharomyces, or picchia or saccharamycodes.

Other alkaline material may be used for the liming operation in step C, including hydroxides of lithium, sodium, ammonium, calcium or potassium. The choice of alkaline material is not critical.

For the salts of aluminum or iron added in step B, the acetate, nitrate, chloride, sulfate or nitrite salts are suitable. In general mineral acid or organic acid salts are suitable for this purpose. Known flocculation agents may be used for this purpose.

In step F, a variety of different organic or mineral acids may be used including tartaric, saccharic, nitric or phosphoric acids.

For the neutralization step G, when the pH is under 7, the hydroxides of sodium lithium, potassium, ammonium, calcium and the like may be used. When the pH is over 7, mineral or organic may be used, such as sulfuric, hydrochloric, nitric, phosphoric and acetic acids.

According to the research performed for the treatment of the invention, the operations listed above need not be followed in the sequence shown. In this process, the term "purified beer" is intended to mean the liquid resulting after the treatment, which presents a low content of substances that will be separated by the distillation, as slops.

After the treatment, the "purified beer" is distilled, with separation of alcohol and of a slop whose contents fall within the conditions prescribed for avoiding pollution at its point of disposal.

The several operations of the treatment are adjusted, for each case, in such a way as to adequately limit the distillation slop content, so that the disposal of this slop will not cause pollution problems in the environment to which it is discharged. Thus, the treatment operations are adjusted in a way suitable to have BOD, COD, phosphor and nitrogen concentrations, etc. within the limits satisfactory for each case. The operating conditions for the several treatment operations will vary, as a conseqence of the adjustment of the treatment, to be made as required in each case in view of the properties of the raw material to be processed, and of the properties of the slops needed for each specific situation in order to avoid pollution problems.

It is to be understood that the sequence of operational steps may be changed in order to arrive at the most economical processing conditions for each type of fermented mash. Depending upon the specific raw material selected for use in the process, the nature of the fermented mash will very greatly. Therefore, a large number of changes may be made in the reaction sequences.

Generally, the process comprises a flocculation of the fermented mash, a settling step and a separation of the liquid alcohol as by distillation. The step of liming may be carried out before or after the flocculation and it is useful to carry out a step of settling after the liming step as well. When aeration is used it is useful to do this prior to flocculation.

The following examples illustrate, but do not limit the described invention.

EXAMPLE 1

In this example, a fermented sugar juice is employed which is obtained by alcoholic fermentation of juice from CB 45-3 variety sugar cane, from Campos campos county area in Brazil. The juice having been extracted by the classical milling process with three mills. To this fermented juice or "beer" which has a pH of 5.5, a saturated solution of aluminum sulfate is progressively added to reach a 1.5% (by weight) concentration of aluminum ion. Then a commerical polyelectrolyte is added in suitable concentration, up to 3 PPM. After this, the liquid is vigorously stirred until it becomes homogeneous and presents peculiar characteristics. During the stirring, the temperature is maintained at 31.5° C. by either heating or cooling the liquid, as may be required. The liquid is then fed into a settler, for continuous settling with a minimum residence time of 2 hours. Next, the supernatant liquid passes to a clarifier, where clarification by liming is made, comprising addition of milk of lime under controlled conditions, until a pH of 9 is reached, subsequent heating to 105° C. under pressure, and settling of the precipitated material. The cleared supernatant liquid of the settler is then cooled to 20° C. in a cooler and goes to a tank where alcohol is added to reach a concentration of 50% per volume of alcohol. In this tank the solids insoluble in alcohol are precipitated.

The liquid is then fed to the distillation column. The stillage from this column is clear and presents a BOD below 3000 mg/l.

EXAMPLE 2

In this example, a fermented sugary juice is used, which is obtained by alcoholic fermentation of a starchy suspension produced by the comminution of cassava previously saccharified with amilase (alpha and beta) type enzymes. The fermented juice ("beer"), which has a pH of 3, is fed into a continuous settler, for settling with a minimum residence time of 2.5 hours.

The supernatant liquid is then passed to a clarifier where clarification by "liming" is performed, comprising addition of milk of lime under controlled conditions until a pH of 10.5 is reached, subsequent heating to 90° C., and settling of the precipitated material.

To the cleared supernatant liquid, aluminum sulfate is added until a concentration of 0.8% (by weight) of aluminum ion is reached. Then the liquid is vigorously and quickly stirred and fed to a continuous settler, for settling of precipitates with a minimum time of residence of 40 minutes.

The liquid is then fed to the distillation column. The stillage from this column is clear and presents a B.O.D. below 3500 mg/l.

EXAMPLE 3

In this example a sugary juice is used, which is obtained by alcoholic fermentation of a molasses solution prepared by adding water to molasses until a sugar concentration of approximately 12% is reached.

At the time the alcoholic fermentation, effected at pH 4.5, is nearly ended, (with juice density changing less than 0.2% in 3 hours) sterilized air is bubbled through the "beer" at 32° C. for 60 hours. This causes the yeast (saccharomyces cerevisiae) to enter a reproductive cycle, at which it digests organic products existing in the "beer". After this aeration, a saturated solution of ferric sulfate is added to the beer until a concentration of 1.2% (in weight) of ferric ions is reached. Then a commercial polyelectrolyte is added in suitable concentration, up to 3 ppm. Any suitable polyelectrolyte of which there are many on the market may be used for the purpose of this invention. The liquid is then vigorously stirred, until it becomes homogeneous and presents peculiar characteristics. The stirring is done quickly, at 32° C.

The liquid is then fed to a settler, for continuous settling, with a minimum residence time of 4.5 hours. Next the supernatant liquid passes to a clarifier, where clarification by "liming" is performed, comprising addition of milk of lime under controlled conditions, until a pH 9 is reached; subsequent heating to 105° C. temperature, under pressure, and settling of the precipitated material takes place. After leaving the clarifier, the liquid is flashed and then cooled to 25° C. This is followed by complete neutralization with sulfuric acid, employing a 20% sulfuric acid solution. Then alcohol is added to reach a concentration of 50% in volume of alcohol. At the same time, tartaric acid is added in a stoichiometric quantity corresponding to the potassium concentration existing in the liquid. While alcohol and tartaric acid are added, a quick vigorous stirring of the liquid is carried out. The liquid is then fed to a continuous settler where the precipitates settles with a minimum residence time of 40 minutes. The supernatent liquid is filtered, completely neutralized by adding sodium hydroxide, and fed to the distillation column. The stillage from this column is a clear yellowish liquid, with B.O.D. lower than 4000 mg/l.

As described in the examples, the claimed process generally comprises the steps of flocculation of the fermented mash, settling the flocculated mash and distillation of the supernatent liquid. In further detail, the process comprises flocculation, liming, settling and distillation. Additionally, settling may be carried out after the flocculation step. Alternatively, aeration may be carried out before flocculation, which is then followed by settling, liming, settling and distillation.

A further alternative resides in first liming the fermented mash, then flocculating, settling and distilling.

In still further detail, the claimed process comprises adding an aluminum or iron salt to flocculate the "beer" or fermented mash, settling and decanting, liming to an alkaline pH, heating to a temperature in the range of 85° C. to 110° C., preferably 90° C. to 105° C., settling again, cooling the supernatant liquid to 15° C.-25° C., adding alcohol to reach at least 50% ethyl alcohol by volume, precipitating and distilling the supernatent liquid to recover the alcohol. An example of this embodiment is in example 1.

In an alternative embodiment the mash after fermentation is permitted to settle and the supernatant liquid is limed to an alkaline pH. After heating to 85°-110° C., the supernatant liquid is flocculated as by addition of an aluminum salt or iron salt or other flocculating agent. After more settling, the liquid is distilled to recover the alcohol product. This embodiment is illustrated in example 2.

As a still further embodiment of the invention, the beer may be first aerated and then flocculated, settled and the supernatant liquid then limed, heated to 85°-110° C. and then flashed, cooled to 15° C.-25° C. and neutralized. Alcohol may then be added as necessary to bring the volume concentration up to about 50%. Tartaric or other acid may be added to precipitate unwanted salts such as potassium. After filtration and neutralization, the alcohol may be recovered. This is illustrated in example 3.

The process herein described presents the following advantages:

1. The process avoids formation of vinasse, which because of its polluting effects cannot be discharged into the environment and for which the existing treatment processes are uneconomical.

2. The wastes resulting from distillation in this process, do not present the polluting effects of vinasse.

3. The settled material separated by decantation in the treatment phase, is easily filterable, with separation of a paste which can be dryed with low energy expenditure. After drying, a solid is obtained which can be used as a component for complex fertilizers or for livestock food.

4. The treatment is economical, as the cost of the required equipment and chemical substances is low.

5. The distillation of the "purified beer", resulting from the treatment of the fermented mash, will be cheaper than the distillation presently used because the "purified beer" feeds the distillation still with controlled chemical characteristics and pH. This brings about lower corrosion, allowing use of cheaper materials for the distillation still. Also it allows to use indirect heating at the still, giving a more economical heat balance.

6. The process avoids polymerization (caramellization), partial carbonization and decompositions of products, which occur at the distillation of the fermented mash and which contribute to give the vinasse its polluting characteristics.

7. The process can be used for new fuel alcohol plants and also at the existing plants, by adapting the existing installations.

Further embodiments will be apparent to those skilled in the art from a consideration of the foregoing specification.

We claim:

1. A process for the production of fuel alcohol, without producing vinasse as an undesirable byproduct, from fermented plant mashes comprising after fermentation of said mashes and before distillation the fermented mash is treated by at least two of the operations listed below, which may be applied in the indicated sequence or in different sequences (a to f):
   (a) adding chemical nutrient substances and oxygen to the fermented mash in an amount sufficient to cause biological digestion of digestable substances in the fermented mash,
   (b) adding a sufficient amount of a flocculating agent to cause flocculation of said fermented mash;
   (c) treating with an alkaline material at temperatures from 60° C. to 105° C. in an amount sufficient to cause reaction with soluble compounds not eliminated by steps (a) and (b);
   (d) decanting solids in suspension with removal and filtration of the sediment, separating and returning to the flow the liquid part obtained after said filtration;
   (e) precipitating substances by addition of alcohol to the liquid, with subsequent separation of salts;
   (f) adding an acid to the liquid to precipitate insoluble salts and subsequently neutralizing;
   and thereafter distilling to recover alcohol from said liquid.

2. The process as claimed in claim 1, wherein aluminum or iron salts are added as the flocculating agent at a proportion between 0.01% and 4%.

3. The process as claimed in claim 1, wherein a polyelectrolyte is used together with the flocculating agent.

4. The process as claimed in claim 1, wherein the alkaline material is calcium or ammonium hydroxide at a proportion between 0.02% and 4%.

5. The process as claimed in claim 1, wherein the alkaline is added to produce a pH between 7 and 12.

6. The process as claimed in claim 1, wherein tartaric acid is used in step (f).

7. The process as claimed in claim 1, wherein the fermented plant mashes are obtained from sugar cane; sugar beets; sorghum starchy materials: manioc, potatoes, corns, wheat, rye; hydrolized cellulosic materials: eucalyptus, pine, or sugar can bagasse.

8. The process as claimed in claim 1, wherein the process is carried out using mashes fermented by the classical batch fermentation process, or fermented mashes resulting from the Melle-Boinot fermenting process (with re-use of the yeast), or resulting from continuous fermentation processes.

9. The process as claimed in claim 1, wherein the process further comprises forming a fermented plant mash, adding a flocculating agent to said mash to flocculate said mash, treating said flocculated mash with an alkaline material, settling said mash into a precipitate and a supernatant liquid, treating the supernatant liquid with an alkaline material, permitting the treated liquid to settle and thereafter distilling to obtain alcohol.

10. The process as claimed in claim 1, wherein the process further comprises forming a fermented plant mash, adding an aluminuma or iron salt to the mash to flocculate the fermented mash, permitting the flocculated mash to settle, decanting the supernatant liquid formed as a result of the settling of the mash, adding lime to the supernatant liquid in a sufficient amount to obtain an alkaline pH, heating said supernatant liquid to a temperature in the range of 85° to 110°, permitting the liquid to settle, cooling the liquid to a temperature in the range of 15° C. to 25° C., adding alcohol in the amount sufficient to obtain at least 50% ethyl alcohol by volume, precipitating insoluble ingredients and distilling the supernatant liquid formed as a result of the precipitation to recover the ethyl alcohol.

11. The process as claimed in claim 1, wherein the process further comprises forming a fermented plant mash, permitting the mash to settle thereby forming a precipitate and a supernatant liquid, liming the supernatant liquid to obtain an alkaline pH, heating the supernatant liquid to a temperature of 85° to 110° C. and flocculating said liquid by the addition of aluminum salt or iron salt, permitting the flocculated liquid to settle, removing the supernatant liquid and distilling to recover the alcohol as a product.

12. The process as claimed in claim 1, wherein the process further comprises forming a fermented plant mash, aerating said mash, adding a flocculating agent to flocculate said mash, permitting the flocculated mash to settle to thereby form a supernatant liquid, liming the supernatant liquid, heating the supernatant liquid to a temperature of 85° to 110° C., cooling the liquid to a temperature of 15° C. to 25° C. and neutralizing said liquid, adding alcohol to bring the volume concentration up to about 50%, adding acid to form a precipitate, filtering said precipitate and neutralizing the liquid obtained as a result of the filtration and distilling the alcohol from said liquid.

* * * * *